United States Patent [19]

Snyder

[11] 4,141,361
[45] Feb. 27, 1979

[54] EVACUATOR

[75] Inventor: Harold I. Snyder, Dover, Ohio

[73] Assignee: Snyder Manufacturing Co., Incorporated, New Philadelphia, Ohio

[21] Appl. No.: 254,080

[22] Filed: May 17, 1972

Related U.S. Application Data

[63] Continuation-in-part of Ser. No. 9,610, Feb. 9, 1970, abandoned.

[51] Int. Cl.² ............................................. A61M 1/00
[52] U.S. Cl. .................................................. 128/278
[58] Field of Search ............................... 128/276–278, 128/297–300, 145.7, 281; 417/234, 395, 437, 470, 472, 474, 479, 544, 568

[56] References Cited

U.S. PATENT DOCUMENTS

| 37,677 | 2/1863 | Colvin | 128/281 |
|---|---|---|---|
| 3,058,627 | 10/1962 | Eskridge | 128/278 |
| 3,111,125 | 11/1963 | Schulte | 128/350 |
| 3,115,138 | 12/1963 | McElvenny et al. | 128/278 |
| 3,376,868 | 4/1968 | Mondiadis | 128/278 |
| 3,461,808 | 8/1969 | Nelson et al. | 417/479 |

Primary Examiner—John D. Yasko
Attorney, Agent, or Firm—Olson, Trexler, Wolters, Bushnell & Fosse, Ltd.

[57] ABSTRACT

The disclosed structure comprises a self-contained surgical evacuator for closed wound suction. A fluid container is provided with a resilient structure that includes a diaphragm and which may be actuated to negative pressure applying position. Upon release, return of the resilient structure to normal position draws fluid into the container from a perforated tubing laid into the wound of the patient.

26 Claims, 15 Drawing Figures

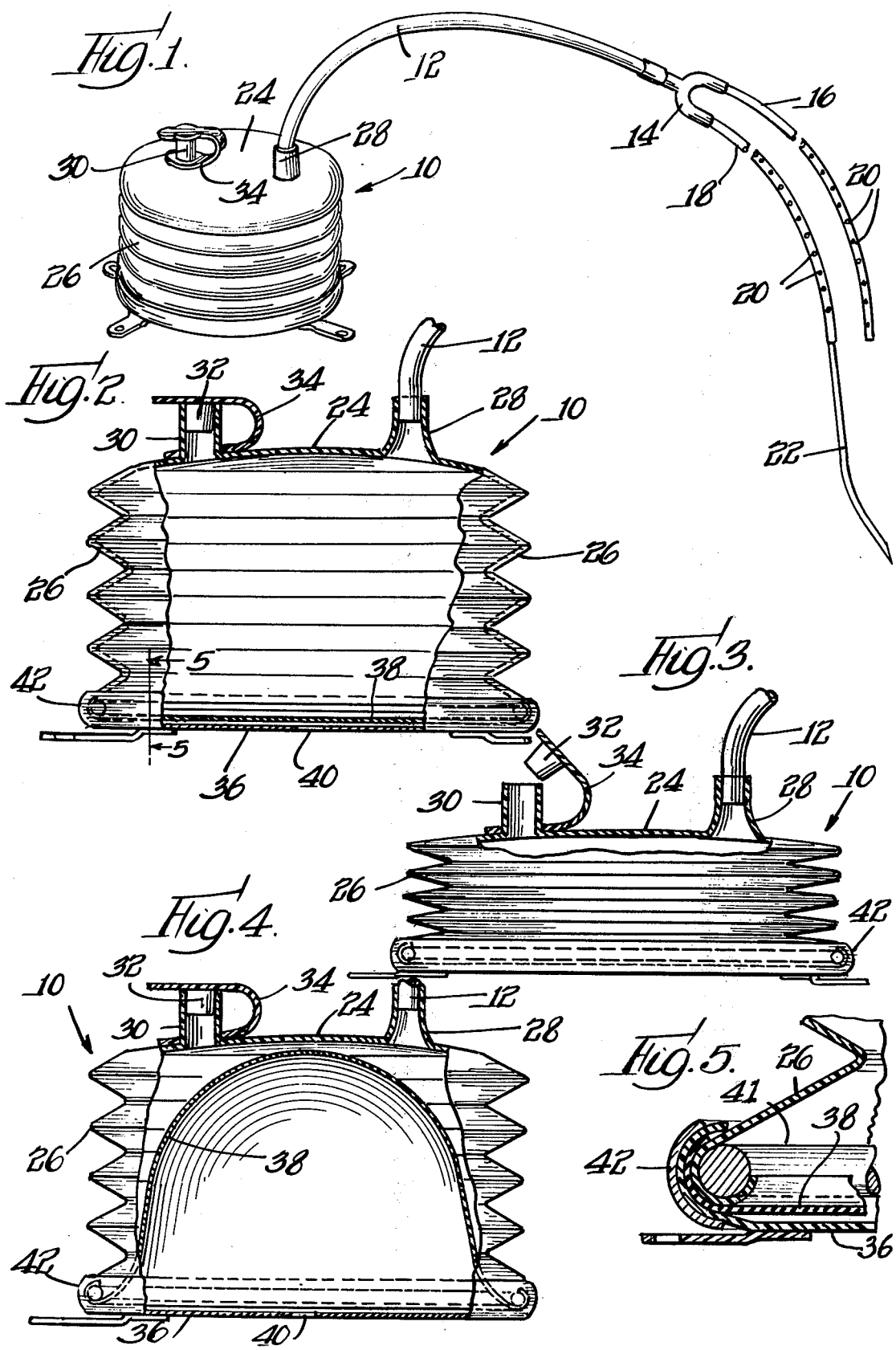

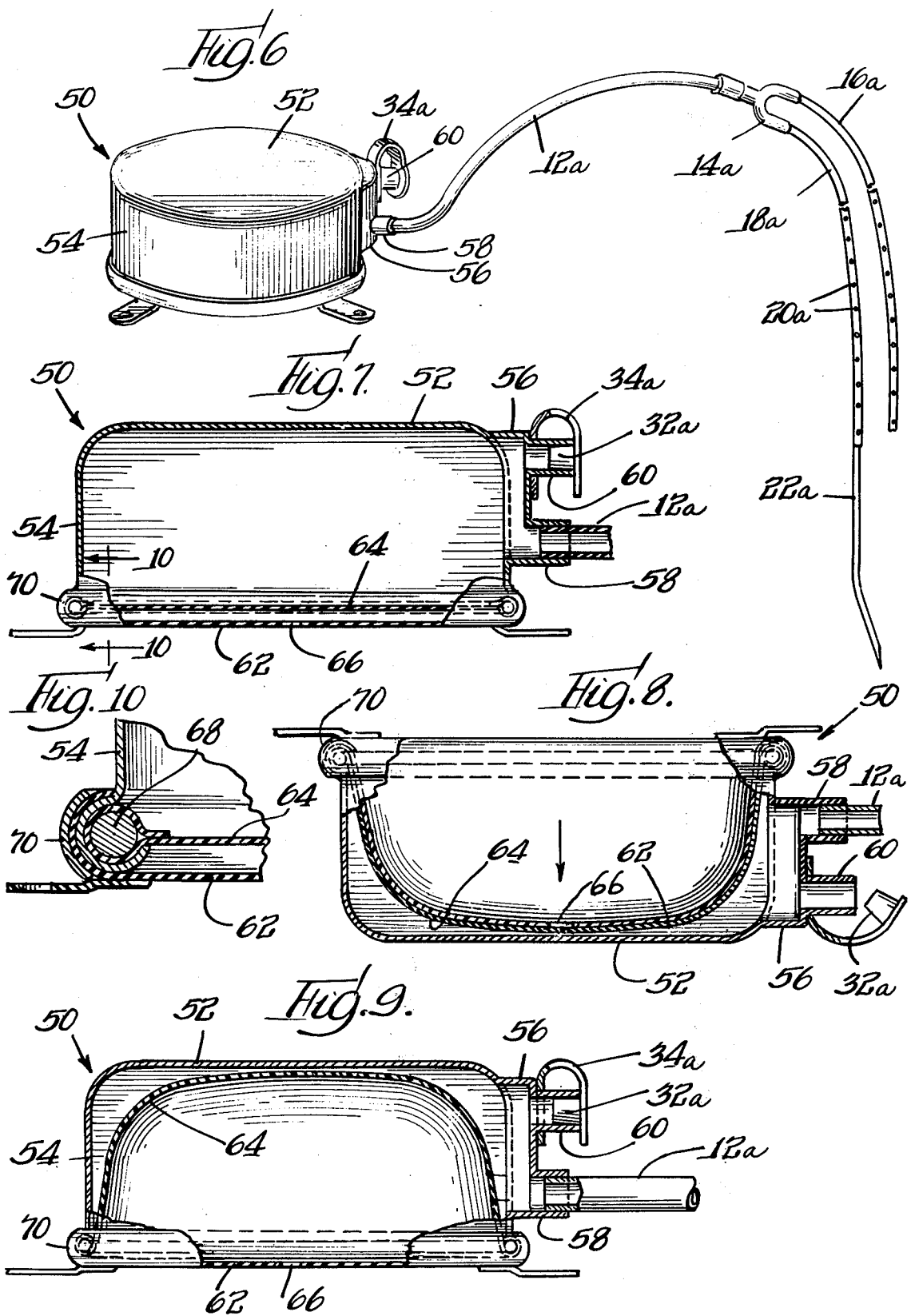

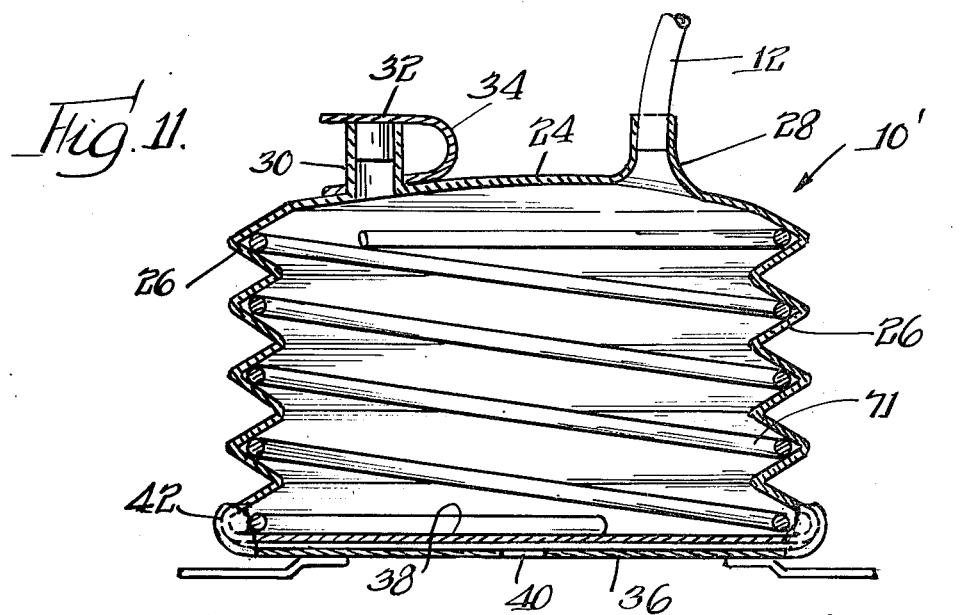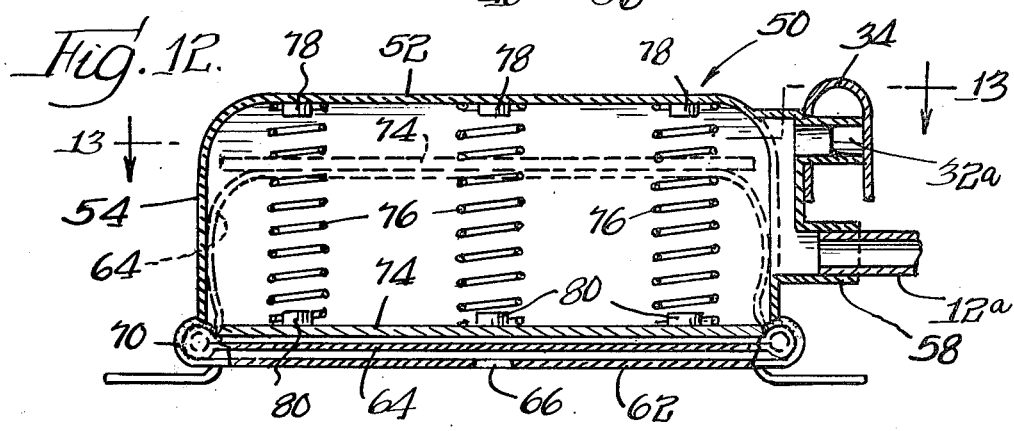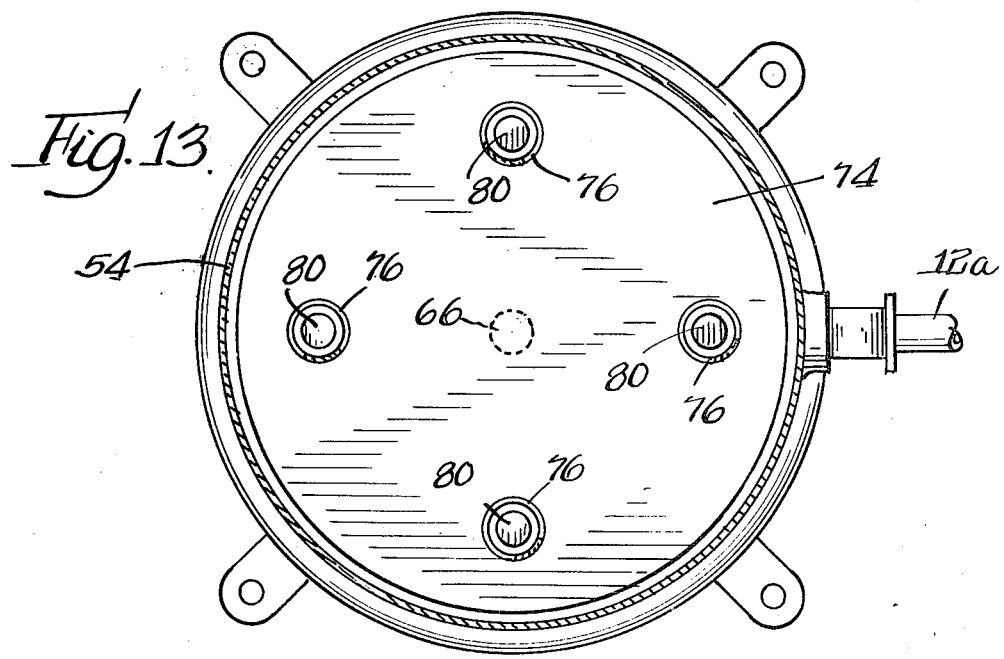

EVACUATOR

This application is a continuation-in-part of my copending application Ser. No. 9,610, filed Feb. 9, 1970, now abandoned.

This invention relates to evacuators, and more particularly to surgical evacuators for the removal of fluid from the human body and the like, of the type and kind set forth in the patent to McElvenny et al. No. 3,115,138, dated Dec. 24, 1963.

The evacuator of said prior patent comprises a container, of predetermined capacity, and adapted for use in the evacuation of fluids from the human body, although of course it may be adapted for other animals use. In said prior patent the container of the evacuator is collapsible, and it is resiliently expansible upon release of a manually applied collapsing pressure, whereby a negative pressure or vacuum of predetermined magnitude may be applied to tubing or the like to which the container is connected. More specifically, the container is arranged for connection to a length of tubing, preferably plastic, of suitable diameter and length; which tubing by means of a suitable "Y" connector or the like, is connected to one or more lengths of plastic tubing, preferably of smaller diameter, and of a type and kind compatible with human body tissue, whereby such smaller tubing may be laid within the wound of a patient for post-operative use. The wound tubing is provided with a multiplicity of small openings of suitable size and in predetermined spaced relation, whereby upon the application of negative pressure to the tubing, fluids will be withdrawn from the wound and the adjacent tissue areas into the tubing, to aid in closing the wound and in removing unwanted fluid, to promote the healing processes. Preferably the wound tubing is adapted for connection with a suitable surgical needle by means of which the tubing may be laid into the wound, and drawn through the body tissue, adjacent to the wound, all as described and set forth in said prior patent.

The container of the evacuator is further provided with an outlet opening, arranged to be closed by a selectively manually operated stopper. The evacuator container may further be provided with support straps, or the like, whereby the container may be conveniently supported upon and carried by the body of the patient.

In use, as set forth in said prior patent, after the wound tubing has been properly laid within the wound of the patient, and the wound sewed up, the stopper for the container outlet is opened or removed and the container collapsed or compressed; whereupon the outlet stopper is replaced, and the container released; whereupon the resilient expansibility of the container applies a negative pressure continuously to the wound tubing and to the wound of the patient, until the container has been filled. There is thus provided a self-contained, independently operable, evacuator for the extraction of body fluids for ambulatory human use.

Subsequent to the issuance of said patent, several patents have been granted, to others, proposing collapsible containers of various types and kinds, generally having as their object, the provision of a container of lower cost. Several of these patents have proposed containers of blow molded plastic construction.

It is an object of the present invention to provide a container, for use in evacuators of the type and kind set forth, which is of lower cost, yet wholly reliable in its operation.

More specifically stated, it is an object of the invention to provide an evacuator container, which itself may or may not be collapsible, but which is provided with a diaphragm arranged to apply the negative pressure, in an economical and reliable manner.

Further objects of the invention are to provide in an evacuator of the type set forth, a container structure which is of simplified construction, which may be readily and economically fabricated, and which may be provided at relatively low cost, but which will be uniform, reliable and accurate in its application of negative pressure to the evacuator structure.

A still further object of the invention is to provide an evacuator container, in at least one embodiment of the invention, which may be used with patients, and in various types of operations, without danger that the container will be inadvertently collapsed by the patient, in use.

Various other objects advantages and features of the invention will be apparent from the following specification wherein certain preferred embodiments are set forth for purposes of illustration.

In the drawings wherein like reference numerals refer to like parts throughout, FIG. 1 is a perspective view of an evacuator having a container constructed in accordance with the present invention, in one of its preferred embodiments.

FIG. 2 is a side elevation of the evacuator container shown in FIG. 1 with its associated elements, upon an enlarged scale; parts of the container being broken away to show elements in section.

FIG. 3 is a view similar to FIG. 2, but illustrating the container in collapsed position.

FIG. 4 is a view, similar to FIG. 2, but showing the diaphragm of the container in activated position for applying a negative pressure.

FIG. 5 is a detail enlarged view, but particularly illustrating the manner of interconnecting the container and the diaphragm, in the form of the invention shown in FIGS. 1-5.

FIG. 6 is a perspective view, similar to FIG. 1, but showing a modified embodiment of the invention.

FIG. 7 is an enlarged side view of the structure of FIG. 6, parts being broken away to show elements in section.

FIG. 8 is a view similar to FIG. 7, but showing the container inverted for activation of the diaphragm.

FIG. 9 is a view similar to FIG. 7, but showing the diaphragm in activated position, for the application of negative pressure.

FIG. 10 is an enlarged detail view more particularly showing the method of interconnecting the container sidewall and diaphragm, in the structure of FIGS. 6-10.

FIG. 11 is an elevational view, partly broken away and in section, of a further modified form of the invention.

FIG. 12 is an elevational view partly broken away and in section, of a further modified form of the invention.

FIG. 13 is a fragmentary sectional view taken along line 13—13 of FIG. 12.

DETAILED DESCRIPTION

Figure 14:
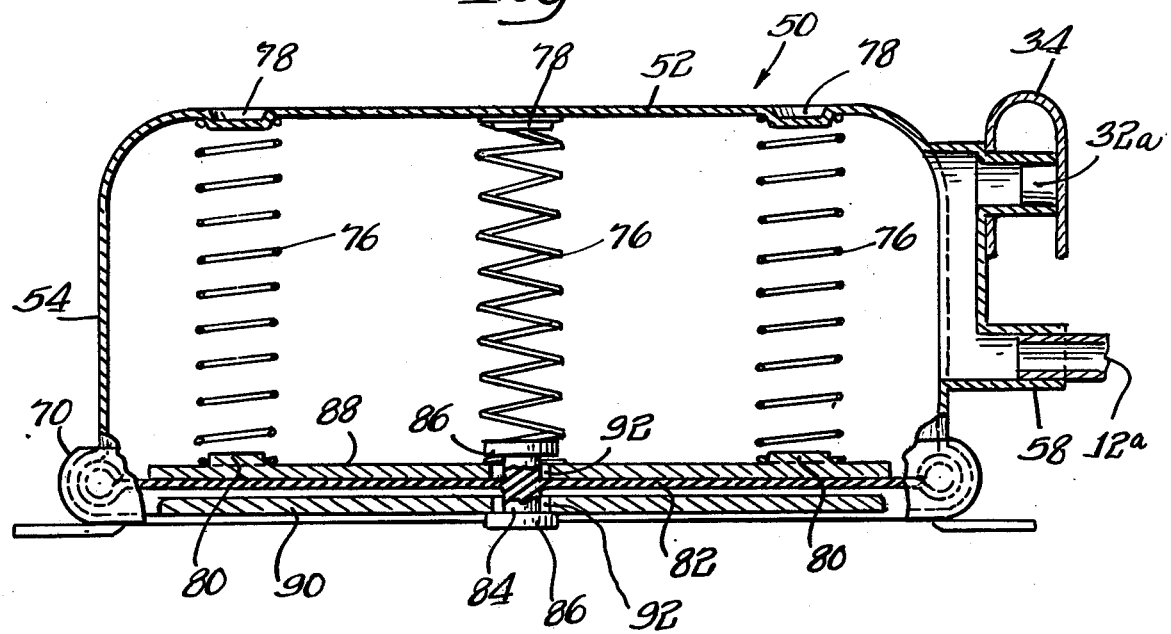
FIG. 14 is an elevational view partly in section and showing a further modification form of the invention.

Referring more particularly to the drawings, and first to the embodiment of the invention illustrated in FIGS. 1–5, there is shown an evacuator of the self-contained, independently operable type comprising a container generally indicated by the reference numeral 10, adapted for interconnection with an inlet tubing 12, preferably of plastic, and of predetermined bore and length. The end of the tubing 12, remote from the container 10, is secured to a "Y" connector 14, to which lengths of wound tubing preferably of smaller diameter, as indicated at 16 and 18, may be connected. As shown, the wound tubing may be provided with a multiplicity of openings or perforations, as indicated at 20; and a surgical needle 22 is shown interconnected with the length of wound tubing 18, all arranged, and for the purpose, as described in said prior U.S. Pat. No. 3,115,138.

As best shown in FIG. 2, the container 10 more specifically comprises a cup-shaped member, of plastic or the like, having a relatively flat topwall 24, and a bellows-like sidewall 26 within which there is formed a plurality of annular bellows-like corrugations. As shown, the sidewall is generally circular in shape, but may be given an oval configuration if desired.

As best shown in FIG. 2, the endwall 24 of the cup-like container body, is provided with a fitting 28 into which the container end of the plastic tubing 12 may be press fitted, and if desired adhesively secured, to provide a fluid-tight connection.

The container wall 24 is also provided with an outlet fitting 30, arranged to be closed by a stopper 32 carried by a strap 34, one end of which is provided with a perforation by means of which the strap may be mounted onto the container fitting 30. As will be understood, the stopper 32 may be selectively applied to and removed from the outlet fitting or opening 30, by manual operation.

The bottom of the cup-like container body is closed by a bottomwall 36, FIG. 2, also preferably of plastic; and within the container, adjacent the bottom thereof, there is disposed a diaphragm member 38. The bottomwall 36 of the container is provided with a central opening or the like, as indicated at 40. Diaphragm 38 is stretched and resilient.

The means for mounting the bottomwall 36, and the diaphragm 38, onto the lower portion of the container sidewall 26, is best shown in FIG. 5. As shown, disposed within the sidewall, adjacent the lower end thereof, there is a relatively rigid metal ring 41 about which the lower end of the sidewall is formed. The container bottomwall 36, and the diaphragm 38, are also formed around the metal ring; and an annular metal ring or fitting 42 is then crimped and clamped around the assembly, so as to hold the parts firmly in position. If desired, adhesive may be laid between the several overlaid parts, as shown in FIG. 5, so as to aid in bonding them together into a fluid-tight connection.

Referring to FIGS. 2, 3 and 4, it will be seen that the stopper 32 may be removed from the container outlet 30, and the container then collapsed as shown in FIG. 3. If the stopper 32 is then re-applied, and the container sidewalls 26 then permitted to re-expand to their normal expanded position, as shown in FIG. 4, it will be seen that the diaphragm 38 will be drawn upwardly, as shown in FIG. 4, into a further stretched or vacuum-applying position. As will be understood, the opening 40 in the container bottomwall 36 permits such operation, the bottomwall thus functioning primarily as a protection for the diaphragm.

It will be seen by reason of the foregoing that a relatively low-cost and reliably operating structure is provided. The main container body, being cup-shaped, may be formed by relatively simple vacuum-forming techniques, as distinguished from more expensive and involved blow molding operations. The entire structure is formed of a relatively small number of parts, which may be easily fabricated and assembled. The collapsible sidewalls 26 of the main container body may be fabricated so that they will collapse upon the application of manual pressure, from the position shown in FIG. 2 to that shown in FIG. 3, then being resiliently expansible to the position of FIG. 4, causing the diaphragm 38 to move to activated position. It will be seen that the action of the bellows walls 26 need not be accurately calibrated viz., it is necessary only that they have sufficient resilient expanding strength to move the structure to the position of FIG. 4, against any retarding influence of the diaphragm 38 as it is drawn into active position. Thus, the main container body may be fabricated of less expensive plastic materials, and the thickness of the sidewall material need not be accurately controlled, as required for example in structures wherein the action of the expanding sidewalls of the container is relied upon to control the applied negative pressure.

In the structure in accordance with the present invention, the application of the negative pressure may be accurately controlled by the action of the diaphragm 38, which may be constructed of resilient material, such as rubber or rubber-like plastic, and accurately rolled or calendared to provide uniformity and predictability in its operation. Thus, the diaphragm 38, which is relied upon to control the accuracy of the applied negative pressure, may be accurately fabricated, but without excessive cost, to facilitate its operation.

In the structure thus provided, it is necessary only that the diaphragm 38 be accurately controlled as to its composition and thickness, to provide a controlled application of negative pressure. As will be understood, the resiliency of the diaphragm 38, as it tends to return from its position as shown in FIG. 4 to the position of FIG. 2, applies a negative pressure or vacuum to the tube 12 to effect the desired evacuator action, as previously described.

In FIGS. 6–10 an embodiment of the invention is illustrated, generally similar to the embodiment previously described, except that in this instance the cup-shaped container body, as indicated generally by the numeral 50, may be of relatively light-weight metal, and of essentially rigid construction.

More particularly, the cup-shaped container body comprises a relatively flat top or endwall 52, and a sidewall 54, generally circular in shape. One portion of the sidewall is provided with an outwardly projecting section or portion, as indicated at 56, upon which is formed a fitting 58, FIG. 7, for connection with the inlet tubing 12a similar in type and kind to the tubing 12 previously described; and with an outlet fitting 60 to which an outlet stopper 32a and a supporting strap 34a may be connected, as in the embodiment previously set forth.

The lower portion of the metal cup-shaped container body is closed by a plastic bottomwall 62, above which is disposed a diaphragm 64, of rubber or the like; except that in this instance the bottomwall 62 may also be formed of rubber, or of a relatively rubber-like plastic, so as to be resiliently flexible in the nature of a rubber diaphragm. The bottomwall 62 is provided with a central opening 66, as in the embodiment previously described.

The manner of securing the parts together is best shown in FIG. 10. As shown, disposed within the lower portion of the cup-like container body is a relatively rigid circular metal ring 68 around which the periphery of the diaphragm 64 may be drawn and adhesively secured. The lower end of the container sidewall 54 is formed around the metal ring 68, as is the periphery of the container bottomwall 62, the parts then being clamped into a rigidly secured connection by means of an encompassing metal ring or fitting 70. As in the embodiment previously described, adhesive may be laid between the laminated parts, to ensure the provision of a fluid-tight connection.

In use, the container body may be inverted from its FIG. 7 position to the position shown in FIG. 8, the outlet stopper 32a removed, and the diaphragms 62 and 64 manually depressed or actuated into the position shown in FIG. 8. Upon re-application of the outlet stopper 32a, and release of the parts, the diaphragms 62 and 64 will move into the position shown in FIG. 9, the diaphragm 64 being thus activated into a negative pressure applying position. As in the embodiment previously described, the diaphragm 64 by its resiliency tends to return to its normal position, as shown in FIG. 7, thereby applying a controlled negative pressure to the tube 12a until the container has been essentially filled.

It will be seen that in the embodiment of the invention illustrated in FIGS. 6-10, inasmuch as the container body is essentially rigid, inadvertent collapse of the container, as for example if the patient should roll onto it, is precluded.

As will be understood, in the embodiment of FIGS. 1-5, the container body 10 may be made of transparent material so that the position of the diaphragm may be observed to determine that it is in active position. Similarly the cover sheet 36 in FIGS. 1-5, or cover sheet 62 in FIGS. 6-10 may be made transparent for the same purpose. Or the cover sheets may be omitted entirely as their use is optional.

FIG. 11 shows a further modified form of the invention which is similar to the form of FIGS. 1-5 and wherein like reference numerals indicate like parts. However, in FIG. 11 a coil-compression spring 71 is mounted in the container 10'. The coils of the spring may lie within the corrugations of the sidewall 26 which in this instance are helically disposed. This coil spring 71 applies forces tending to expand the container 10' and may be useful in evacuators where the plastic of the container does not have sufficient strength or resiliency to maintain the container in its expanded condition or to cause the container to expand after it has been collapsed.

Thus, upon collapsing the container 10' in a manner illustrated in FIG. 3, the coil spring 71 collapses. Upon release of the container the coil spring 71 expands the container 10' whereby the diaphragm 38 assumes a position similar to that shown in FIG. 4 to apply controlled negative pressure. Depending upon the stiffness of a diaphragm 38 and that of the spring 71, the container may not fully expand following collapse thereof. In such case the negative pressure is applied to the combined action of the spring 70 and diaphragm 38.

FIGS. 12 and 13 show a further modified form of the invention which is similar to the form of FIGS. 6-10 and wherein like reference numerals indicate like parts. In FIGS. 12 and 13 a circular disc 74 of metal or plastic is disposed within the container body 50 and generally parallel to the top and bottom walls 52, 62. The disc 74 is of smaller diameter than the inside diameter of the sidewall 54 so as to be movable within the container body 50. One or more coil compression springs 76 are disposed between the top wall 52 and disc 74. In the form shown four springs 76 are used. The springs 76 may be maintained in their operative positions by bosses 78, 80 suitably provided on the top wall 52 and disc 74. In addition, it should be noted, that the bottom wall diaphragm 62 may be eliminated, or it may be used in this form of the invention as a protector for the diaphragm 64.

When the diaphragm 64 (and diaphragm 62 if used) are depressed with the outlet stopper 32a removed, the disc 74 compresses the springs 76, and the parts of the unit assume positions shown in broken lines, FIG. 12. The diaphragm 62 lies against the disc 74 whereby the disc 74 serves as a backing for the diaphragm. This is useful in constructions where the diaphragm 64 is thin and may lose some of its elasticity when stretched. Consequently, the resiliency of the diaphragm 64 alone is not relied upon to provide the controlled negative pressure, as aforesaid, but functions in conjunction with the springs 76 to apply such negative pressure.

Figure 15:
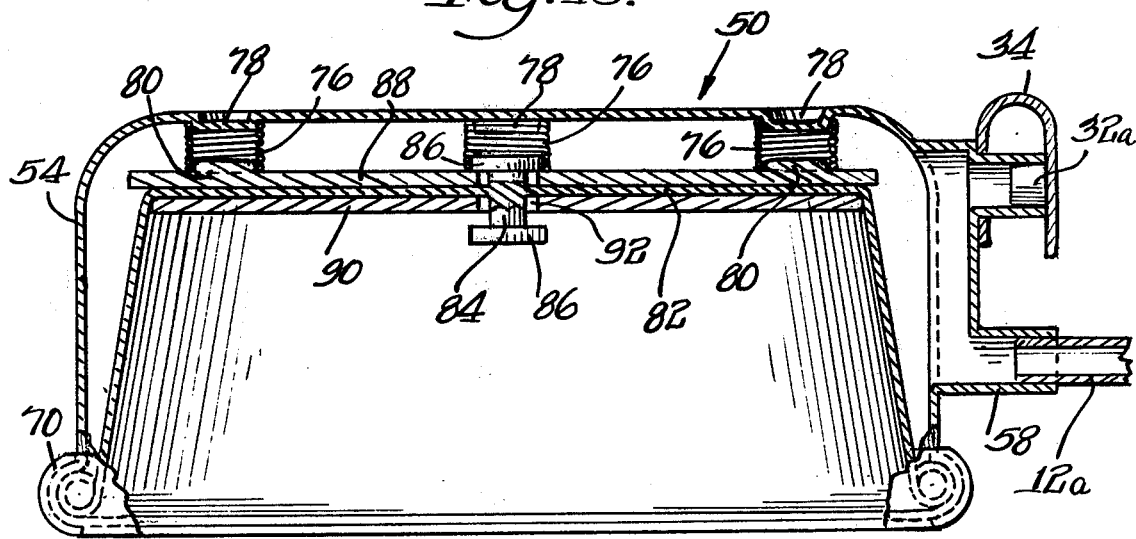
FIG. 15 is a view similar to FIG. 14 but showing the unit activated for the application of negative pressure.

In the modification shown in FIGS. 14 and 15, like reference numerals indicate like parts in FIGS. 12 and 13. However, in the form of the invention in FIGS. 14 and 15, the resilient diaphragm 82 is integrally formed centrally thereof with an axial stem 84 having enlarged resilient heads 86, 86 spaced from respective adjacent surfaces of the diaphragm 82. Discs 88, 90 of substantially rigid plastic are disposed against the inner and outer surfaces of the diaphragm 82. Outer disc 90 may be somewhat smaller in diameter then inner disc 88. The discs 88, 90 each have a central hole 92 that is smaller then the diameter of the heads 86 but larger than the diameter of stems 84 proper. Thus, each disc 88, 90 may be snapped over one of the heads 86, 86 so as to be retained thereby. The inner disc has four bosses 80 for anchoring the ends of springs 76 as in FIGS. 12 and 13.

When the outlet stopper 32a is removed and manual pressure is applied to the outer disc 90, the springs 80 are compressed and the parts of the evacuator assume the positions shown in FIG. 15. Controlled negative pressure is applied to the interior of the container body by the combined action of the springs and diaphragm. The outer disc 90 is particularly useful in distending the diaphragm 82. Since manual pressure is applied by the disc 90 over a large area of the diaphragm 82, it is possible to obtain a greater reduction of volume of the container body than if no outer disc were used. Consequently, the container has more capacity for storage of evacuated body fluid.

The invention is claimed as follows:

1. A self-contained, independently operable, evacuator for the extraction of body fluids, for ambulatory human use, said evacuator comprising in combination, a container, a resilient diaphragm formed as a movable end wall of said container with its outer face open to atmosphere, said diaphragm having a normal position which it tends to assume by reason of its resiliency across one end of the container and being operable upon the manual actuation thereof to a stretched negative pressure applying position within the container confines and toward the opposite end thereof with the outer face of the diaphragm remaining open to atmosphere during this movement, said container being provided with an opening into which a conduit of flexing tubing may be connected, the other end of said tubing being of a material compatible with human tissue and being arranged for insertion into a body wound, whereby as said diaphragm returns to normal position across the said one end of the container the negative pressure applied by the diaphragm within the container will effect the extraction of body fluids from the wound by continuous suction, said fluids being thereby expressed into the container for storage therein.

2. An evacuator as defined in claim 1 wherein said container is resiliently compressible by manual actuation to effect the movement of said diaphragm to negative pressure applying position.

3. An evacuator as defined in claim 1 wherein said container is rigid and said diaphragm is movable therein.

4. An evacuator as defined in claim 1 wherein said container is provided with means including a valve forming an outlet for said container.

5. An evacuator as defined in claim 4 wherein said valve is selectively manually controlled.

6. An evacuator as defined in claim 1 wherein said diaphragm comprises a sheet-like member of flexible resilient material.

7. An evacuator as defined in claim 6 wherein there is provided a flexible apertured wall adjacent the outer face of the diaphragm.

8. A self-contained, independently operable, evacuator for the extraction of the body fluids, for ambulatory human use, said evacuator comprising in combination, a container, resilient means including a diaphragm formed as a movable end wall of said container with its outer face open to atmosphere, said diaphragm having a normal position which it tends to assume by reason of the action of said resilient means across one end of the container and being operable upon the manual actuation thereof to a negative pressure applying position within the container confines and toward the opposite end thereof stressing the resilient means with the outer face of the diaphragm remaining open to atmosphere during this movement, said container being provided with an opening into which a conduit of flexing tubing may be connected, the other end of said tubing being of a material compatible with human tissue and being arranged for insertion into a body wound, whereby as said diaphragm returns to normal position across the said one end of the container the negative pressure applied by the resilient means within the container will effect the extraction of the body fluids from the wound by continuous suction, said fluids being thereby expressed into the container for storage therein.

9. An evacuator as defined in claim 8 in which said resilient means is formed by resilient material of said diaphragm.

10. An evacuator as defined by claim 8 in which said resilient means includes spring means in said container.

11. An evacuator as defined by claim 9 in which said container has substantially rigid cup-shaped body.

12. An evacuator as defined by claim 9 in which said container has a collapsible boby.

13. An evacuator according to claim 12 having spring means in said body tending to expand the same.

14. An evacuator according to claim 11 in which said resilient means includes a disc for applying pressure to said diaphragm, and spring means for imposing pressure on said disc.

15. An evacuator according to claim 8 in which said resilient means includes discs on the inner and outer faces of said diaphragm, and spring means for imposing pressure on the disc that is on said inner face.

16. An evacuator as defined in claim 1 wherein the container includes peripheral wall means extending from said one end of the container to the opposite end thereof with the diaphragm disposed within the peripheral wall means and toward the opposite end of the container when in negative pressure applying position.

17. An evacuator as defined in claim 8 wherein the container includes peripheral wall means extending from said one end of the container to the opposite end thereof with the diaphragm disposed within the peripheral wall means and toward the opposite end of the container when in negative pressure applying position.

18. An evacuator as defined in claim 1 wherein said diaphragm comprises a sheet-like member of flexible resilient material and wherein there is provided an apertured wall adjacent the outer face of the diaphragm.

19. A self-contained, independently-operable surgical evacuator unit adapted to drain fluid from a body site and to transfer fluid to the unit, said unit comprising:
  (A) a cup formed of rigid material and having a continuous side wall and an unbroken end wall,
  (B) an elastic membrane covering the cup and sealed to the lip thereof to define a sump chamber to hold fluid, said membrane in its unstretched state being substantially planar,
  (C) an inlet-exhaust fixture mounted on said side wall and communicating with said chamber, said fixture when functioning in an inlet mode being adapted for connection to a drain tube leading to a body site to be drained, said fixture also being arranged to function in an exhaust mode, and
  (D) an actuator member associated with said membrane and manually-operable by an inwardly-directed force to effect inward stretching of said membrane to displace the atmosphere of said chamber through said fixture in the exhaust mode and to create in the inlet mode of said fixture a negative pressure acting to draw fluid into said chamber when the member is released, said membrane then being capable of returning to its original unstretched state without the use of an external force whereby fluid withdrawn from the body site proceeds to fill said chamber.

20. A surgical evacuator unit as set forth in claim 19, wherein said inlet-exhaust fixture is constituted by separate fixture elements mounted on said side wall, said exhaust fixture having means to effect opening and closing thereof.

21. A unit as set forth in claim 19, wherein said cup is formed of transparent plastic material.

22. A unit as set forth in claim 19, wherein said cup is provided with a flange encircling the lip thereof to facilitate strapping said unit to a patient.

23. A unit as set forth in claim 22, wherein said membrane is clamped and sealed between said flange and a locking ring telescoping within said side wall.

24. A unit as set forth in claim 19, wherein said membrane is formed of rubber.

25. A unit as set forth in claim 20, wherein said exhaust fixture is provided with a removable stopper plug.

26. A unit as set forth in claim 20, wherein said exhaust fixture is provided with a valve to effect opening and closing thereof.

* * * * *